United States Patent [19]

Andersen

[11] 4,165,502

[45] Aug. 21, 1979

[54] CURRENT LIMITER ASSEMBLY FOR A CIRCUIT BREAKER

[75] Inventor: Paul R. Andersen, Cedar Rapids, Iowa

[73] Assignee: Square D Company, Park Ridge, Ill.

[21] Appl. No.: 804,693

[22] Filed: Jun. 8, 1977

[51] Int. Cl.$^2$ .............................................. A01H 75/10

[52] U.S. Cl. .......................................... 335/39; 337/78

[58] Field of Search ........................... 335/39, 16, 195; 337/70, 75, 85, 78

[56] References Cited

U.S. PATENT DOCUMENTS 3,943,473 3/1976 Khalid .................................... 335/16

4,071,836 1/1978 Cook et al. ........................ 335/16 X

*Primary Examiner*—George Harris

*Attorney, Agent, or Firm*—Norton Lesser; Larry I. Golden; Richard T. Guttman

[57] ABSTRACT

The following specification describes a bimetal in the limiter assembly of a circuit breaker to operate the trip crossbar for opening the main circuit breaker contacts. An arm is also provided on one blade of the current limiter contacts to also operate the trip crossbar for ensuring rapid opening of the main contacts of the circuit breaker in response to high fault currents. The bimetal is connected between the electromagnet winding and one of the current limiter contact blades in shunt with a path of selected resistance. The resistance is selected as desired by connecting pigtail conductors of desired size either in shunt with or to selected portions of the bimetal to control the current passing through the bimetal for controlling the heat of the bimetal in accordance with the rating of the breaker. A calibration assembly for the bimetal is carried by the electromagnetic assembly.

19 Claims, 7 Drawing Figures

CURRENT LIMITER ASSEMBLY FOR A CIRCUIT BREAKER

BACKGROUND OF THE INVENTION

Field of the Invention

This invention relates in general to circuit breaker trip arrangements and more particularly to improved or more economical apparatus utilizing a current limiter assembly for operating a circuit breaker trip crossbar.

Summary of the Prior Art

Several conventional techniques are used in circuit breakers for sensing the presence of overcurrents. One is the use of a magnetic assembly for responding to the magnetic field generated by the overcurrent to operate a trip bar. Another is the use of a bimetal which is deflected by the heat of the overcurrent to operate the trip bar. The operated trip bar in turn releases the operating assembly of the circuit breaker to open the main contacts of the breaker.

In circuit breakers having a relatively low ampere rating the bimetal is actually in the circuit extending through the breaker and for circuit breakers having high ampere ratings the bimetal is indirectly heated by attachment to a portion of one of the circuit elements commonly known as a heater, which increases in temperature as the current increases. In the latter case current does not pass directly through the bimetal.

Both systems require a relatively high resistance either in the resistance of the bimetal itself or by the circuit element to which the bimetal is attached in order to provide sufficient thermal energy to deflect the bimetal. This resistance effect can cause the breaker to exceed the allowable or safe temperature rise even if carrying a rated current.

In U.S. Pat. No. 3,943,473 and related patents, a current limiter assembly for a circuit breaker is disclosed utilizing a pair of current limiter contacts in series with the main contacts of the circuit breaker. The current limiter assembly includes an electromagnetic assembly having a low resistance winding in series with the circuit breaker contacts and which responds to extremely high fault currents for separating the current limiter contacts. In this arrangement no means were provided under direct control of the current limiter assembly for ensuring that the main contacts of the circuit breaker were opened by the magnetic assembly responsive to high fault currents.

SUMMARY OF THE INVENTION

In the present invention, it is proposed to provide sufficient thermal energy to the bimetal to operate the trip bar without altering the overall resistance of the circuit breaker by simply utilizing a selected portion of the bimetal in a shunt path with the circuit breaker current limiter components to utilize only a selected small portion of the total circuit breaker current. This provides sufficient current to enable calibration of the bimetal and operation of the trip bar at a desired operating current.

To provide this function a portion of the bimetal is connected in a shunt path of selected resistance between the electromagnetic assembly and one of the current limiter blades of the current limiter assembly functioning in a manner similar to that described in the aforementioned patent. One end of the bimetal is supported by the electromagnetic assembly and pigtail conductors are connected between the electromagnetic assembly and a selected portion of the bimetal and between the bimetal and the blade, while the blade is also connected directly to the electromagnetic assembly over a pigtail conductor of a selected size to provide a shunt path. The shunt path ensures that for example, only 10% of the current passing through a circuit breaker rated at 225 amps will provide sufficient thermal energy to enable calibration of the bimetal without interfering with the circuit breaker normal current operation. The resistance of the shunt path may be varied as needed to select the required conditions for operating the bimetal dependent on the rating of the circuit breaker. Since a higher percentage of the total current is required to be passed through the bimetal for lower rated breakers in order to maintain proper calibration simply changing the pigtail between the electromagnetic assembly and the blade will pass the desired percentage of total energy through the bimetal. For lower rated breakers all of the current may be passed through the bimetal. the bimetal is also protected from high fault currents by the transfer of current from the blade through the PTC resistor when the electromagnetic assembly operates to open the current limiter contacts.

A calibration screw and spring for calibrating the bimetal are supported by the electromagnetic assembly and an arm is also provided on the current limiter contact blade to operate the trip bar directly in response to operation of the current limiter contact blades.

It is therefore an object of the present invention to provide an improved and more economical method and/or apparatus for utilizing a bimetal in a circuit breaker.

It is another object of the present invention to utilize a current limiter assembly of a circuit breaker for controlling a bimetal to operate a trip bar.

It is still another object of the present invention to provide an improved and more economical bimetal calibration and trip bar operating arrangement for a circuit breaker.

Other objects and the features of the present invention will become apparent on examination of the following specification and claims together with the accompanying drawings.

DESCRIPTION OF THE PREFERRED EMBODIMENT

Figure 1:
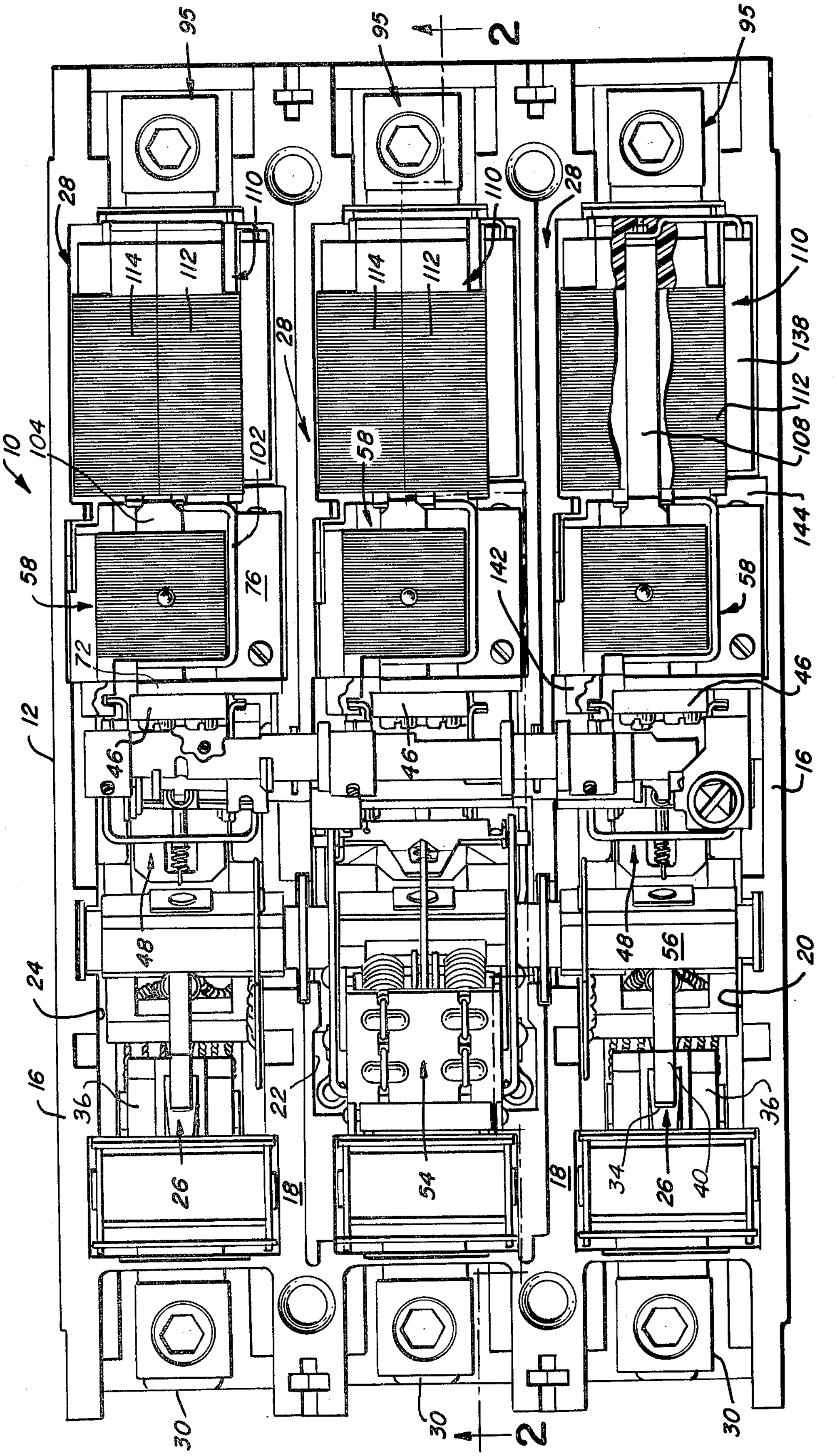
FIG. 1 is a top elevational view of the base of a molded case current limiting circuit breaker incorporating the principles of the present invention.
Figure 2:
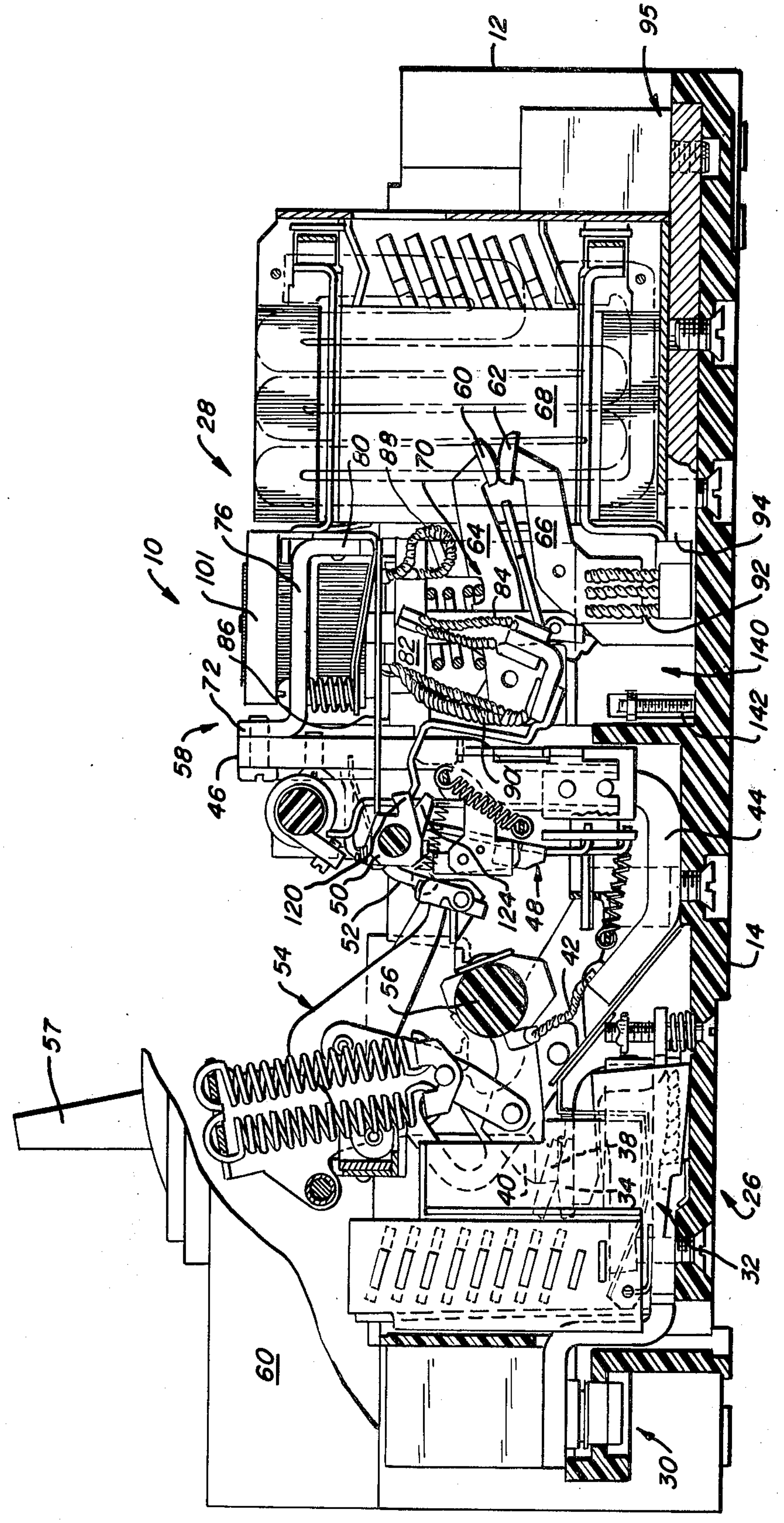
FIG. 2 is a sectional view taken generally along the line 2—2 in FIG. 1 showing a portion of a cover.
Figure 7:
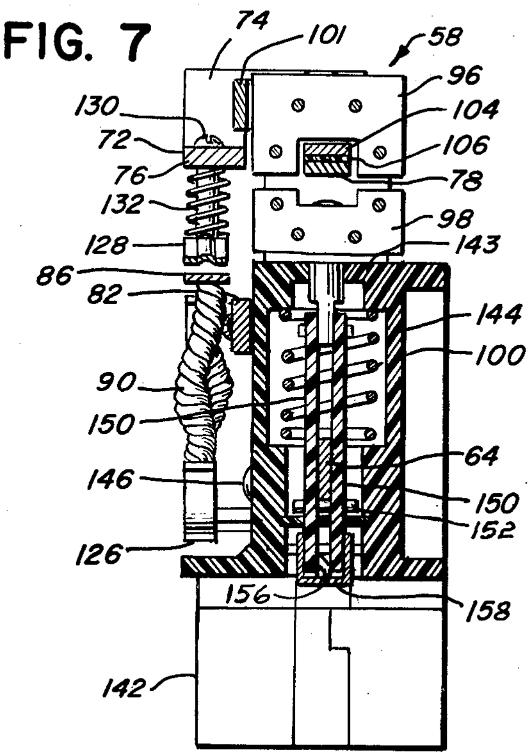
FIG. 7 is a sectional view taken generally along the line 7—7 in FIG. 3.
Figure 6:
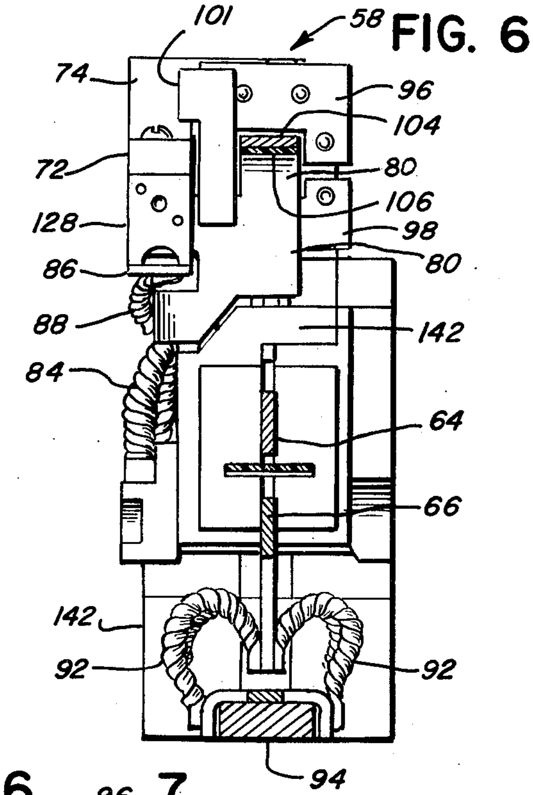
FIG. 6 is a sectional view taken generally along the line 6—6 in FIG. 3.

In FIGS. 1 and 2 the relevant portion of a multi-pole current limiting circuit breaker for use in a three phase circuit is indicated generally by the reference character 10.

The circuit breaker 10 includes a molded base 12 having a back or bottom wall 14, longitudinally extending side walls 16 and a pair of spaced barrier or compartment walls 18 located intermediate the side walls 16 to define three longitudinally extending compartments 20, 22 and 24 seen in FIG. 1. Each compartment 20, 22 and 24 has a circuit breaker assembly 26 as shown and described in copending application Ser. No. 804,694 filed simultaneously June 8, 1977 herewith by Andersen and Kramer and a current limiter assembly 28.

The circuit breaker assembly 26 includes a line terminal portion 30 adjacent one compartment end for conventionally connecting a respective line conductor (not shown) through a blade assembly 32. The assembly 32 includes a contact 34 supported on a blade engaged by the back leg of a spring biased U shaped arc suppression magnet 36 as explained in the aforementioned application. Contact 34 is engaged by contact 38 on blade 40 to form the main contacts of the circuit breaker and blade 40 is connected via a flexible braided conductor 42 to a conductor 44 located adjacent the bottom wall 14 of the base 12 and having a vertically extending leg 46 adjacent the central vertical axis of the breaker.

The circuit breaker section further includes a magnetic assembly 48 in each compartment 20, 22 and 24 for operating trip crossbar 50 in response to an overcurrent fault condition. Magnetic assembly 48 is substantially as shown and described in the aforementioned copending application. The operated trip bar 50 has a latch plate to conventionally release the latch 52 of an operating assembly 54 in the circuit breaker center section 26 to pivot a blade crossbar 56. Blade crossbar 56 pivots blade 40 in each compartment to separate main contacts 34 and 38 for opening the circuit between terminal portion 30 and conductor 44. The operating assembly 54 may thereafter be conventionally operated by means of a handle 57 extending through a cover 60 partially shown in FIG. 2 for resetting contacts 34 and 38 and reengagement with the trip bar, when the fault condition is corrected.

The current limiting assembly 28 includes an electromagnetic assembly 58 in each compartment for opening a respective pair of separable current limiter contacts 60 and 62 carried by blades 64 and 66 respectively and located in a respective arc extinguishing chamber 68. The blade 64 is moved by an armature assembly 70 of the electromagnetic assembly 58 in response to a predetermined minimum high fault or short circuit current passing through conductor 44 and leg 46 to a conductive member 72 of the electromagnetic assembly 58 and exceeding a selected overcurrent condition operating the magnetic assembly 48.

Figure 3:
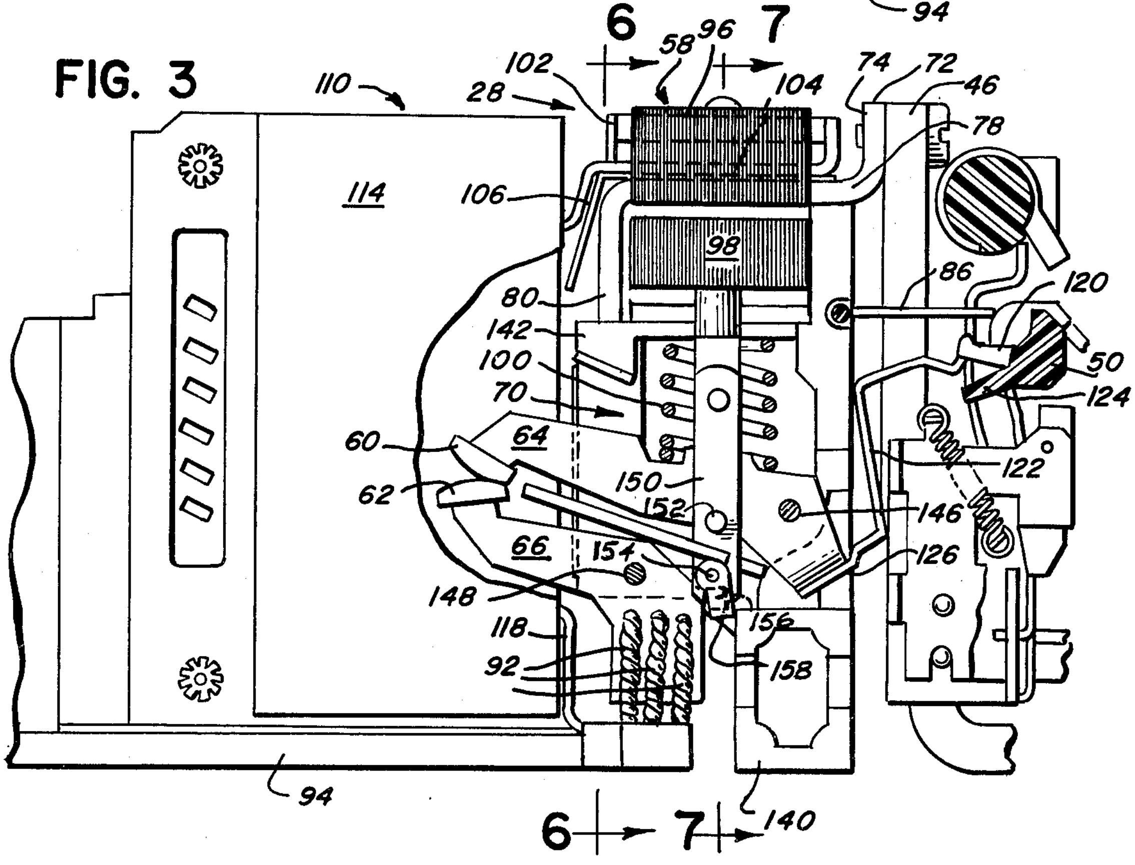
FIG. 3 is a side elevational view of the electromagnetic assembly shown in FIG. 1 in partial section with a portion of the housing removed.
Figure 5:
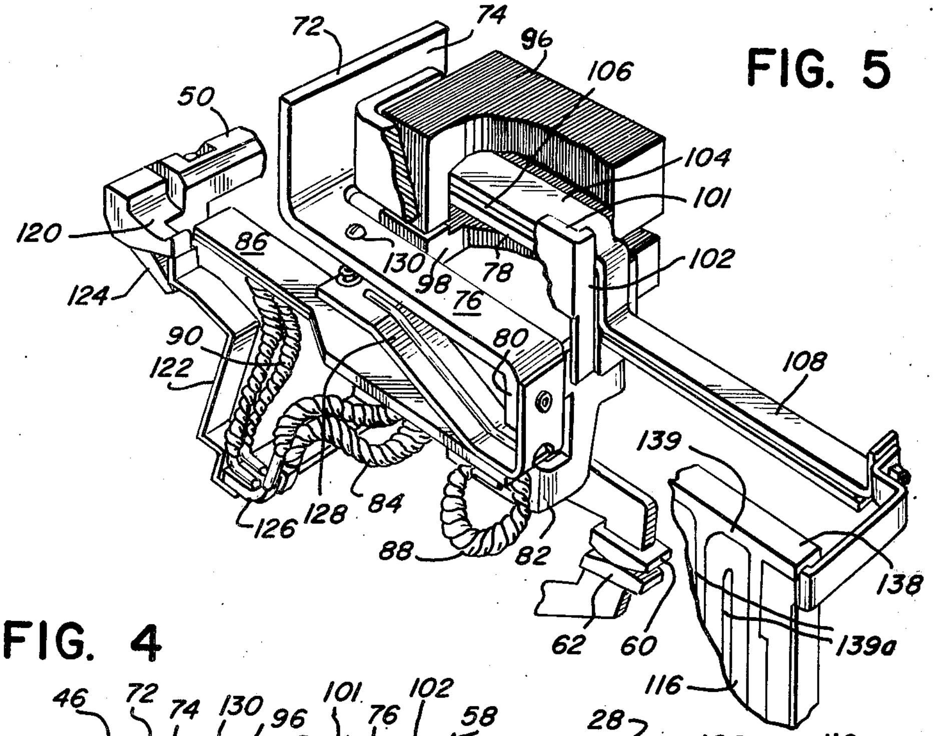
FIG. 5 is an isometric view of a portion of the electromagnetic and bimetal assembly.
Figure 4:
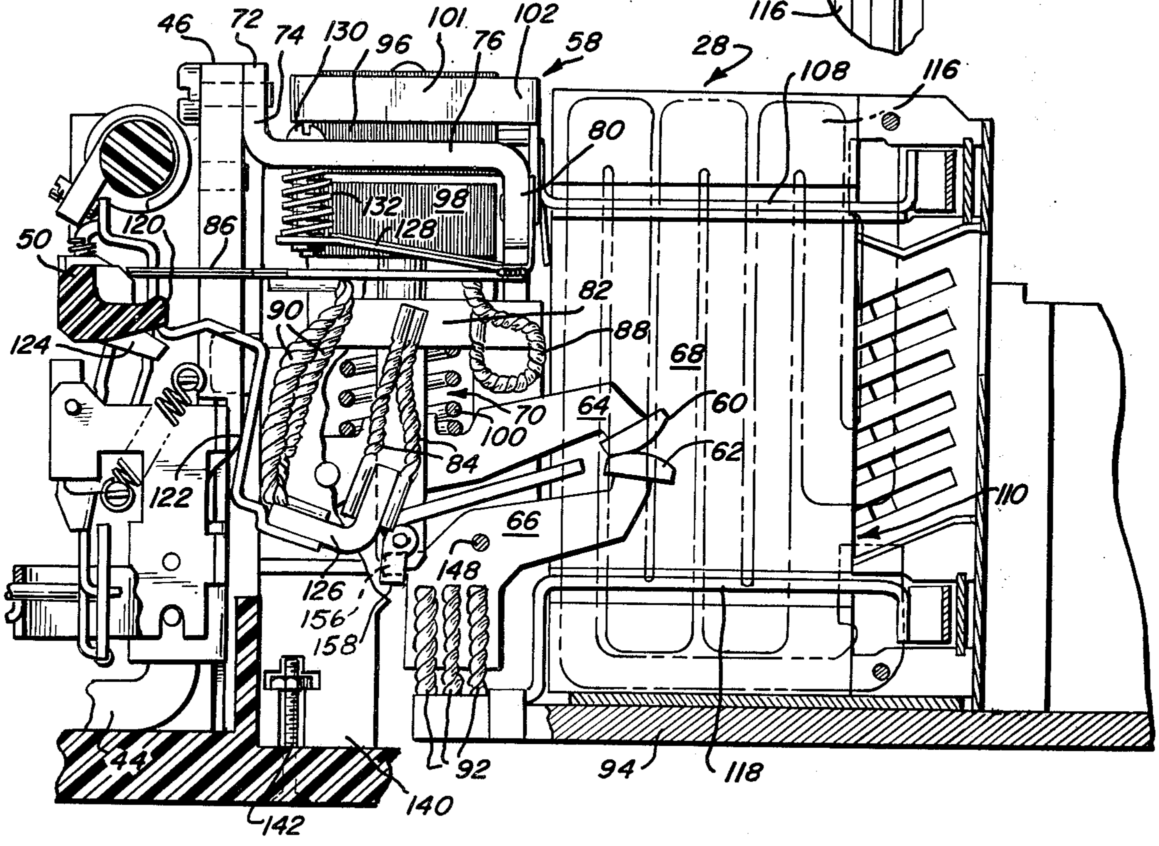
FIG. 4 is a side elevational view of the electromagnetic assembly taken in a direction opposite FIG. 3 with only a portion of the housing shown.

The conductive member 72 has a right angle tab 74 secured to conductive leg 46 and from which two spaced parallel legs 76 and 78 extend to an integrally formed bar 80 spaced from tab 74, as best seen in FIGS. 3–5. Bar 80 has an integrally formed depending L shaped tang 82 connected to blade 64 via a plurality of flexible braided pigtail conductors 84 in shunt with a bimetal strip 86. Bimetal strip 86 is secured to bar 80 and is connected to tang 82 by a plurality of braided pigtail conductors 88 and to blade 64 via a plurality of braided pigtail conductors 90. Conductors 88 and 90 are connected at selected positions along the bimetal strip 86 to form a path of selected resistance in shunt with conductors 84. Thus either the number and size of conductors 84 or alternatively conductors 88 and 90 and the length of bimetal therebetween are selected to control the percent of current passing through the bimetal 86.

Blade 64 of course extends the circuit from terminal 30 and conductor leg 46, through member 72 to blade 66 and through flexible braided conductors 92 to a bar conductor 94 adjacent the bottom wall extending to a terminal assembly 95 for connection to an external conductor (not shown).

Electromagnetic assembly 58 includes a U shaped magnetic core 96 formed by a plurality of magnetically permeable laminations and defining a passage through which leg 78 of member 72 extends. Core 96 is effective for controlling armature assembly 70 to move blade 64 for separating contacts 60 and 62, as described in the aforementioned patent and includes a plurality of magnetically permeable laminations forming a U shaped armature 98 biased by a coil or helical spring 100 for closing contacts 60 and 62. The legs of U shaped armature 98 are spaced adjacent and facing the legs of U shaped core 96.

The bar 80 interconnecting one end of legs 78 and 76 is also secured to a tang depending from one leg 101 of a U shaped member 102. Leg 101 extends adjacent core 96 intermediate and above legs 76 and 78 toward tab 74 and the back leg of member 102 interconnects leg 101 with leg 104 which seats between the legs of core 96 in aligned parallel relationship with leg 78 and separated therefore by an insulating member 106. Leg 104 serves to assist in holding contacts 60 and 62 open as explained in the aforementioned patent and is connected by a downwardly extending tang to a winding leg 108 for a field magnet assembly 110.

As explained in the aforementioned patent the field magnet 110 comprises a pair of members 112 and 114 formed of magnetically permeable laminations and defining the arc suppression chamber 68 encircling the blades 64 and 66. The winding leg 108 is connected to one terminal of a PTC resistor 116 formed of iron, for example. The other terminal of resistor 116 is connected through a field magnet winding leg 118 which connects to conductor 94 adjacent conductors 92. The field magnet assembly 110 functions as described in the aforementioned patent to quench the arc generated between opening contacts 60 and 62, while the current is transferred through the resistor 116, which heats to provide a high resistance holding down the high fault current.

Bimetal strip 86 extends to a position adjacent a trip lug 120 of trip bar 50 for the purpose of operating bar 50, when the strip 86 is deflected from a calibrated position. Blade 64 also has an L shaped lever 122 for engaging a trip lug 124 of the trip crossbar 50 for operating the bar 50 as soon as blade 64 moves. Lever 122 is secured to blade 64 at an offset position therefrom and from the bar operating end of strip 86 by a crossarm 126 of blade 64. Conductors 84 and 90 are also actually connected to arm 126 of blade 64.

Conductors 88 as mentioned are connected between a selected portion of the bimetal strip 86 and tang 82 and the conductors 90 are connected between another selected portion of the strip 86 and the crossarm 126 of blade 64. Thus a portion of the current which would normally pass from tang 82 to blade 64 is shunted through the bimetal strip 86. The proportion of shunted current may of course be varied by selecting the length of bimetal between conductors 88 and 90 or conveniently by number, size or diameter of conductors 84. Controlling the size of conductors 84 has the effect of shunting a larger or smaller proportion of current from the bimetal, which may therefore be utilized to provide a desired resistance and/or to draw a selected heat energy in accordance with the breaker rating and in desired instances the conductors 84 are entirely omitted. Examples of breaker ratings for different diameters or areas of conductors 84 are provided below:

| Breaker Rating | Conductor 84 cross section in sq. inches |
|---|---|
| 225 amps | .0245 |
| 200 amps | .0103 |
| 175 amps | .00513 |
| 150 amps | .00323 |
| 125 amps | .00203 |
| 110 amps | 0 |

A desired portion of the total available energy is therefore passed through strip 86 as needed to be provided for controlling the operation of trip bar 50 in response to a selected overheat condition.

To calibrate the bimetal strip for operating the trip bar 50 in response to a selected overheat condition, a calibration strip 128 is secured to strip 86 and has tang for riveting to bar 80. A screw 130 is threaded through leg 76 and strip 128 to position the strip 86 at a desired position relative lug 120 to operate bar 50 in response to a selected thermal or overheat condition. Spring 132 is provided to take up any back lash in the screw movement.

In normal operation current flows between terminals 30 and 95 connected to conductor 94 through a low resistance circuit including contacts 34 and 38, conductor 44, conductive segment 72, connected to blade 64 through conductors 84 in shunt with conductors 88, bimetal 86 and conductors 90 and from blade 64, through contacts 60 and 62, blade 66 and conductors 92 to conductor 94. The relatively high resistive circuit through conductive legs 101, 104, 108, PTC resistor 116, and conductive leg 118 is connected in shunt with conductor 82, the shunt combination at conductor 84 and bimetal 86, and contacts 60 and 62 and therefore no consequential current flows through the PTC resistor during normal operation.

Current flow in a thermal range of an overheat condition will of course cause the bimetal strip 86 to engage lug 120 and operate the trip bar 50. A moderate overcurrent condition operates the magnetic assembly 48 which engages a respective trip lug to operate the trip bar 50. In either event, the operated trip bar 50 releases operating assembly 54 which causes contacts 34 and 38 to open for interrupting the circuit between terminal 30 and conductor 94. On clearing the fault condition, handle 58 is moved to control the operating assembly 54 and reset contacts 34 and 38 for again completing the circuit between terminal 30 and conductor 94.

On the occurrence of a high fault current of the type such as occurs on a short circuit and which may be in the neighborhood of 100,000 amps, current flow through the winding leg 78 of the electromagnetic assembly generates a magnetic field for attracting armature assembly 70 against the bias of coil spring 100. The current through blades 64 and 66, which form partial turns for field magnet 110, generates a magnetic field to assist in separating the blades. The separating force is proportional to the square of the current so that high short circuit currents increase the rate of contact separation.

Lever 122, which moves immediately with blade 64 is provided to operate the trip bar 50 substantially instantaneously with the movement of blade 64 in response to a high fault current. Trip bar 50 thus ensures the opening of contacts 34 and 38 within a short time span.

As the contacts 60 and 62 separate, a larger portion of current flows through segments 101, 104 and 108, PTC resistor 116, and through winding 118 is shunt with the arc current between contacts 60 and 62 as the resistance of the arc path increases to extinguish the arc. Leg 104 then becomes effective to hold contacts 60 and 62 open in conjunction with the field generated by the winding legs of the field magnet.

With current flowing through PTC resistor 116, it heats rapidly to limit the fault current, while the main contacts 34 and 38 are opening to interrupt all current. After the fault condition is cleared, handle 57 is operated as before described to reset the contacts 34 and 38 so that the circuit between terminal 30 and conductor 94 is again established.

It will be noted that the PTC resistor 116 is formed in a serpentine shape and is encapsulated in a shallow recess of a housing 138 formed by a substantially planar wall with a rim 139 and spaced ribs 139*a* to inhibit arcing across adjacent resistor segments. Each housing 138 is received between a respective compartment wall and one external vertical face of a respective adjacent magnet member of chamber 68. A terminal extending from opposite ends of resistor 116 at right angles to the main plane of housing 138 is provided for connection to ends of legs 108 and 118 respectively. This serves to provide a compact space saving and economical arrangement for the current limiter assembly.

A further improvement is provided by an insulating housing 140 supporting the armature assembly 70 and blades 64 and 66. The housing 140 comprises blocks 142 and 144 having a recess in which the spring 100 is seated and nestingly receiving the blades 64 and 66 therebetween with a pivot pin 146 for blade 64 and a pivot pin 148 for blade 66 extending into both blocks 142 and 144. The blocks are provided with interlocking tabs and recesses and form a bottom planar surface seated on wall 14 and secured thereto. It will be noted that the block 142 has an L shaped upper end with a vertical leg seated under tab 74 and the other leg forms a shelf 143 spaced below armature 98. A passage in the shelf 143 receives a rod attached to armature 98 and is in turn attached to a pair of insulating links 150 encircled by spring 100. Spring 100 seats in a recess between the blocks 142 and 144 and biases blade 64 counterclockwise about pin 146, as seen in FIG. 3. A pin 152 extending through links 150 and in contact with the under side of blade 64 thus tends to drive links 150 down. However, another pin 154, extending through links 150 and in contact with a tab 156 off the back of blade 66, tends to drive blade 66 clockwise about pin 148 until contact 62 touches contact 60 on blade 64. Since blade 64 is tending to rotate counterclockwise about pin 146, a static blade and link position is defined to accomodate contact erosion or wear. When links 150 are driven up by the action of electromagnet assembly 58, pin 152 moves blade 64 clockwise, while U shaped member 158 attached to pin 154, moves blade 66 counterclockwise to open contacts 160 and 162.

The electromagnetic assembly 58 together with housing 142 are faciley assembled as a unit to the field magnet assembly 110, the PTC resistor 116 in housing 138 and the terminal 95. The housing 142 together with the attached apparatus is then simply inserted in base 12, secured to bottom wall 14 and conductors 46 and 72 connected together.

A tab on block 142 engages over an ear of the magnetic assembly 64 as explained in the aforementioned application to maintain the magnetic assembly seated in its recess.

The invention is not believed to be limited to the particular embodiments hereinbefore described but is believed set forth in the accompanying claims.

What I claim is:

1. A current limiting assembly for a circuit breaker having a pair of serially connected main circuit breaker contacts operable to an open position in response to the movement of a trip bar in response to either an overheat or overcurrent condition, the improvement comprising:
   - a pair of current limiting contacts,
   - an electromagnet assembly including a low resistance winding connected to said main contacts and operable in response to a high fault current for opening said current limiting contacts, and
   - a bimetal serially connected between said winding and one of said current limiting contacts for responding to an overheat condition to move said trip bar for opening said main contacts.

2. A current limiting assembly for a circuit breaker having a pair of serially connected main circuit breaker contacts operable to an open position in response to the movement of a trip bar in response to either an overheat or overcurrent condition, the improvement comprising:
   - a pair of current limiting contacts,
   - an electromagnet assembly including a low resistance winding connected to said main contacts and operable in response to a high fault current for opening said current limiting contacts,
   - a bimetal serially connected between said low resistance winding and one of said current limiting contacts for responding to an overheat condition to move said trip bar for opening said main contacts, and
   - means serially connected between said low resistance winding and said one current limiting contact and in shunt with said bimetal with said means having a resistance selected to enable opening of said main circuit breaker contacts in response to an overheat condition.

3. The assembly claimed in claim 2 in which said means comprises a pigtail conductor of a size corresponding to the rating of the breaker for enabling said bimetal to pass a selected percentage of the current passing through said main contacts.

4. A current limiting assembly for a circuit breaker having a pair of serially connected main circuit breaker contacts operable to an open position in response to the movement of a trip bar in response to either an overheat or overcurrent condition, the improvement comprising:
   - a pair of current limiting contacts,
   - an electromagnet assembly including a low-resistance winding connected to said main contacts operable in response to a high-fault current for opening said current limiting contacts,
   - a bimetal serially connected between said winding and one of said current limiting contacts for responding to an overheat condition to move said trip bar for opening said main contacts, and
   - a resistor having a positive temperature coefficient of resistance connected in shunt with said current limiting contacts for passing said high fault current in response to the opening of said current limiting contacts.

5. In the assembly claimed in claim 4, a planar wall for supporting said resistor independently of said breaker, and said resistor having a serpentine shape extending substantially parallel to the plane of said wall.

6. A current limiting assembly for a circuit breaker having a pair of serially connected main circuit breaker contacts operable to an open position in response to the movement of a trip bar in response to either an overheat or overcurrent condition, the improvement comprising:
   - a pair of current limiting contacts,
   - an electromagnet assembly including a low resistance winding connected to said main contacts and operable in response to a high fault current for opening said current limiting contacts,
   - a bimetal serially connected between said winding and one of said current limiting contacts for responding to an overheat condition to move said trip bar for opening said main contacts,
   - a blade supporting said one current limiting contact and moved in response to energization of said winding by said high fault current for opening said current limiting contact, and
   - means moved with said blade for moving said trip bar to open said trip bar to open said main contacts.

7. In the assembly claimed in claim 6 an armature assembly for said winding adapted to move said blade in response to energization of said winding by said high fault current, and a housing carrying said armature assembly and blade independently of said breaker.

8. In the assembly claimed in claim 6 in which said winding includes a conductor integrally joined at opposite ends to a shunt leg, and means for supporting said bimetal at one of said ends.

9. In the assembly claimed in claim 8, a pigtail conductor connecting said one end to said bimetal at a selected position on said bimetal, and another pigtail conductor connecting another selected position on said bimetal and said blade.

10. For use in a circuit breaker having a pair of serially connected main circuit breaker contacts operable to an open position in response to the movement of a trip bar and having a pair of current limiting contacts adapted to be opened in response to a high fault current passing through an electromagnetic winding connected to said main contacts the improvement comprising:
    - means serially connecting said winding to said current limiting contacts to enable operation of said electromagnetic winding for opening said current limiting contacts in resonse to a high fault current, and
    - a bimetal connected in shunt with said means and passing a selected proportion of the current passing through said current limiting contacts for responding to an overheat condition to move said trip bar for opening said main contacts.

11. In the improvement claimed in claim 10, means operated by said electromagnetic winding in response to a high fault current for moving said trip bar simultaneously with the opening of said current limiting contacts to open said main contacts.

12. The improvement claimed in claim 11 in which said operated means comprises a blade supporting one of said current limiting contacts, and means on said blade for engaging said trip bar in response to movement of said blade for opening said current limiting contacts.

13. The improvement claimed in claim 12 in which said means serially connecting said winding to said current limiting contacts includes a pigtail conductor having a size corresponding to the rating of said breaker.

14. The improvement claimed in claim 13 in which said pigtail conductor has a cross sectional area of 0.0245 square inches for a breaker rating of 225 amperes and a cross sectional area of 0.002 square inches for a breaker rating of 125 amperes.

15. The improvement claimed in claim 14 in which a selected portion of said bimetal is connected to said winding by a pigtail conductor of selected size and another portion of said bimetal is connected to said blade by another pigtail conductor.

16. For use in a circuit breaker having a pair of serially connected main circuit breaker contacts operable to an open position in response to the movement of a trip bar movable in response to either an overheat or an overcurrent condition and including a pair of current limiting contacts adapted to be opened in response to a high fault current passing through an electromagnetic winding connected to said main contacts the improvement comprising:

means serially connecting said winding to said current limiting contacts and having a resistance selected to enable operation of said electromagnetic winding for opening said current limiting contacts in response to a selected high fault current, and means operable in response to the opening of said current limiting contacts for moving said trip bar to open said main contacts.

17. In the assembly claimed in claim 16 a blade carrying over said current limiting contacts and movable in response to the energization of said winding by a high fault current for opening said current limiting contacts, and said means operable in response to the opening of said current limiting contacts includes a lever carried by said blade.

18. In the assembly claimed in claim 17, a bimetal connected in shunt with said means serially connecting said winding to said current limiting contacts and passing a selected proportion of the current passing through said current limiting contacts for responding to an overheat condition to move said trip bar for opening said main contacts.

19. The improvement claimed in claim 1 in which said means serially connecting said winding to said current limiting contacts includes a pigtail conductor having a size corresponding to the rating of said breaker.

* * * * *

UNITED STATES PATENT AND TRADEMARK OFFICE

CERTIFICATE OF CORRECTION

PATENT NO. : 4,165,502

DATED : August 21, 1979

INVENTOR(S) : Paul R. Andersen

It is certified that error appears in the above-identified patent and that said Letters Patent are hereby corrected as shown below:

Col. 2, line 19, change "the" (third occurrence) to -- The --.

Col. 6, line 8, change "is" to --in--.

Col. 8, line 51, change "resonse" to --response--.

Signed and Sealed this

*Thirteenth* Day of *November 1979*

[SEAL]

*Attest:*

RUTH C. MASON
*Attesting Officer*

LUTRELLE F. PARKER
*Acting Commissioner of Patents and Trademarks*